(12) United States Patent
Ishii et al.

(10) Patent No.: US 8,574,574 B2
(45) Date of Patent: Nov. 5, 2013

(54) PHARMACEUTICAL COMPOSITION COMPRISING ANTIBODY COMPOSITION WHICH SPECIFICALLY BINDS TO CCR4

(75) Inventors: Toshihiko Ishii, Shizuoka (JP); Miyoko Asano, Shizuoka (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 221 days.

(21) Appl. No.: 12/879,121

(22) Filed: Sep. 10, 2010

(65) Prior Publication Data

US 2011/0262431 A1    Oct. 27, 2011

Related U.S. Application Data

(60) Provisional application No. 61/241,558, filed on Sep. 11, 2009.

(30) Foreign Application Priority Data

Sep. 10, 2009 (JP) .............................. P. 2009-209218

(51) Int. Cl.
*A61K 39/395* (2006.01)

(52) U.S. Cl.
USPC ..................................... 424/133.1

(58) Field of Classification Search
None
See application file for complete search history.

(56) References Cited

U.S. PATENT DOCUMENTS

| | | | |
|---|---|---|---|
| 2003/0175273 A1 | 9/2003 | Shitara et al. | |
| 2007/0020263 A1* | 1/2007 | Shitara et al. | 424/144.1 |

FOREIGN PATENT DOCUMENTS

| | | | |
|---|---|---|---|
| EP | 1 702 625 A1 | 9/2006 | |
| WO | 03-018635 A1 | 3/2003 | |
| WO | 2005-053741 A1 | 6/2005 | |
| WO | 2008-019378 A1 | 2/2008 | |
| WO | 2008-058021 A2 | 5/2008 | |

OTHER PUBLICATIONS

Wu et al Clinical Cancer Research vol. 14 p. 4650 (2007).*
International Search Report [PCT/ISA/210], issued in PCT/JP2010/065566, Nov. 9, 2010.
Asahi Ito, et al.; "Defucosylated anti-CCR4 monoclonal antibody exercises potent ADCC-mediated antitumor effect in the novel tumor-bearing humanized NOD/Shi-*scid*, IL-2R$\gamma^{null}$ mouse model" Cancer Immunol Immunnother, 2009; vol. 58; pp. 1195-1206.
Rinpei Niwa; et al.; "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma"; Cancer Research, Mar. 2004; vol. 64; pp. 2127-2133.
Lei Wu, et al.; "Lenalidomide Enhancement of NK Cell-Mediated Antibody-Dependent Cellular Cytotoxicity (ADCC) Is Mediated by Granzyme B and FasL and is Associated with Modification of SHIP-1, PLC-g2 and pERK and Enhanced Chemokine Production"; Blood (ASH annual Meeting Abstracts); 2007; vol. 110, Abstract 4885; American Society of Hematology; 2 pages total.
European Patent Office, Extended European Search Report, dated Jan. 31, 2013, issued in counterpart European Application No. 10815436.0.

* cited by examiner

*Primary Examiner* — Sheela J Huff
(74) *Attorney, Agent, or Firm* — Sughrue Mion, PLLC

(57) ABSTRACT

A pharmaceutical composition, comprising an antibody composition which specifically binds to human CC chemokine receptor 4 (hereinafter also referred to as CCR4) and at least one medicament; and a pharmaceutical composition for administering in combination of a recombinant antibody against CCR4 and at least one medicament are required. The present invention can provide a pharmaceutical composition comprising a recombinant antibody against CCR4 and at least one medicament; and a pharmaceutical composition for administering in combination of a recombinant antibody against CCR4 and at least one medicament.

6 Claims, 3 Drawing Sheets

```
                         SEQUENCE LISTING

<160> NUMBER OF SEQ ID NOS: 12

<210> SEQ ID NO 1
<211> LENGTH: 360
<212> TYPE: PRT
<213> ORGANISM: Homo sapiens

<400> SEQUENCE: 1

Met Asn Pro Thr Asp Ile Ala Asp Thr Thr Leu Asp Glu Ser Ile Tyr
 1               5                  10                  15

Ser Asn Tyr Tyr Leu Tyr Glu Ser Ile Pro Lys Pro Cys Thr Lys Glu
                20                  25                  30

Gly Ile Lys Ala Phe Gly Glu Leu Phe Leu Pro Pro Leu Tyr Ser Leu
            35                  40                  45

Val Phe Val Phe Gly Leu Leu Gly Asn Ser Val Val Val Leu Val Leu
        50                  55                  60

Phe Lys Tyr Lys Arg Leu Arg Ser Met Thr Asp Val Tyr Leu Leu Asn
    65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
                100                 105                 110

Ile Ser Trp Met Tyr Leu Val Gly Phe Tyr Ser Gly Ile Phe Phe Val
            115                 120                 125

Met Leu Met Ser Ile Asp Arg Tyr Leu Ala Ile Val His Ala Val Phe
        130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
                180                 185                 190

Leu Asn Ser Thr Thr Trp Lys Val Leu Ser Ser Leu Glu Ile Asn Ile
            195                 200                 205

Leu Gly Leu Val Ile Pro Leu Gly Ile Met Leu Phe Cys Tyr Ser Met
        210                 215                 220

Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
                245                 250                 255
```

```
Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Tyr Thr Gln Ser Thr Met
            340                 345                 350

Asp His Asp Leu His Asp Ala Leu
        355                 360

<210> SEQ ID NO 2
<211> LENGTH: 28
<212> TYPE: PRT
<213> ORGANISM: Homo sapiens

<400> SEQUENCE: 2

Asn Pro Thr Asp Ile Ala Asp Thr Thr Leu Asp Glu Ser Ile Tyr Ser
1               5                   10                  15

Asn Tyr Tyr Leu Tyr Glu Ser Ile Pro Lys Pro Cys
            20                  25

<210> SEQ ID NO 3
<211> LENGTH: 18
<212> TYPE: PRT
<213> ORGANISM: Homo sapiens

<400> SEQUENCE: 3

Asp Glu Ser Ile Tyr Ser Asn Tyr Tyr Leu Tyr Glu Ser Ile Pro Lys
1               5                   10                  15

Pro Cys

<210> SEQ ID NO 4
<211> LENGTH: 15
<212> TYPE: PRT
<213> ORGANISM: Homo sapiens
<220> FEATURE:
<223> OTHER INFORMATION: Synthetic Peptide

<400> SEQUENCE: 4

Asp Glu Ser Ile Tyr Ser Asn Tyr Tyr Leu Tyr Glu Ser Ile Pro
1               5                   10                  15

<210> SEQ ID NO 5
<211> LENGTH: 5
<212> TYPE: PRT
<213> ORGANISM: Mus musculus
<220> FEATURE:
<223> OTHER INFORMATION: Synthetic Peptide

<400> SEQUENCE: 5

Asn Tyr Gly Met Ser
1               5

<210> SEQ ID NO 6
<211> LENGTH: 17
<212> TYPE: PRT
<213> ORGANISM: Mus musculus
<220> FEATURE:
```

<223> OTHER INFORMATION: Synthetic Peptide

<400> SEQUENCE: 6

Thr Ile Ser Ser Ala Ser Thr Tyr Ser Tyr Tyr Pro Asp Ser Val Lys
1               5                   10                  15

Gly

<210> SEQ ID NO 7
<211> LENGTH: 10
<212> TYPE: PRT
<213> ORGANISM: Mus musculus
<220> FEATURE:
<223> OTHER INFORMATION: Synthetic Peptide

<400> SEQUENCE: 7

His Ser Asp Gly Asn Phe Ala Phe Gly Tyr
1               5                   10

<210> SEQ ID NO 8
<211> LENGTH: 16
<212> TYPE: PRT
<213> ORGANISM: Mus musculus
<220> FEATURE:
<223> OTHER INFORMATION: Synthetic Peptide

<400> SEQUENCE: 8

Arg Ser Ser Arg Asn Ile Val His Ile Asn Gly Asp Thr Tyr Leu Glu
1               5                   10                  15

<210> SEQ ID NO 9
<211> LENGTH: 7
<212> TYPE: PRT
<213> ORGANISM: Mus musculus
<220> FEATURE:
<223> OTHER INFORMATION: Synthetic Peptide

<400> SEQUENCE: 9

Lys Val Ser Asn Arg Phe Ser
1               5

<210> SEQ ID NO 10
<211> LENGTH: 9
<212> TYPE: PRT
<213> ORGANISM: Mus musculus
<220> FEATURE:
<223> OTHER INFORMATION: Synthetic Peptide

<400> SEQUENCE: 10

Phe Gln Gly Ser Leu Leu Pro Trp Thr
1               5

<210> SEQ ID NO 11
<211> LENGTH: 119
<212> TYPE: PRT
<213> ORGANISM: Artificial Sequence
<220> FEATURE:
<223> OTHER INFORMATION: Synthetic peptide

<400> SEQUENCE: 11

Glu Val Gln Leu Val Glu Ser Gly Gly Asp Leu Val Gln Pro Gly Arg
1               5                   10                  15

Ser Leu Arg Leu Ser Cys Ala Ala Ser Gly Phe Ile Phe Ser Asn Tyr
            20                  25                  30

Gly Met Ser Trp Val Arg Gln Ala Pro Gly Lys Gly Leu Glu Trp Val
        35                  40                  45

-continued

```
Ala Thr Ile Ser Ser Ala Ser Thr Tyr Ser Tyr Tyr Pro Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Leu Tyr Tyr Cys
                 85                  90                  95

Gly Arg His Ser Asp Gly Asn Phe Ala Phe Gly Tyr Trp Gly Gln Gly
                100                 105                 110

Thr Leu Val Thr Val Ser Ser
            115

<210> SEQ ID NO 12
<211> LENGTH: 112
<212> TYPE: PRT
<213> ORGANISM: Artificial Sequence
<220> FEATURE:
<223> OTHER INFORMATION: Synthetic peptide

<400> SEQUENCE: 12

Asp Val Leu Met Thr Gln Ser Pro Leu Ser Leu Pro Val Thr Pro Gly
  1               5                  10                  15

Glu Pro Ala Ser Ile Ser Cys Arg Ser Ser Arg Asn Ile Val His Ile
                 20                  25                  30

Asn Gly Asp Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser Leu Leu Pro Trp Thr Phe Gly Gln Gly Thr Lys Val Glu Ile Lys
                100                 105                 110
```

PHARMACEUTICAL COMPOSITION COMPRISING ANTIBODY COMPOSITION WHICH SPECIFICALLY BINDS TO CCR4

BACKGROUND OF THE INVENTION

1. Field of the Invention

The present invention relates to a pharmaceutical composition, comprising an antibody composition which specifically binds to human CC chemokine receptor 4 (hereinafter also referred to as CCR4) and at least one medicament.

2. Brief Description of the Background Art

The prognosis with T-cell lymphoma is very poor and there is no therapeutic agent which exhibits sufficient drug efficacy. It is known that human CC chemokine receptor 4 is expressed on some kinds of T-cell lymphoma including adult T-cell leukemia/lymphoma, cutaneous T cell lymphoma and the like (Non-patent literatures 1 and 2). Therefore, a pharmaceutical composition comprising an antibody composition which specifically binds to CCR4 can be a pharmaceutical composition effective for treating T-cell tumors which expresses CCR4 (Patent literatures 1, 2 and 3).

Lenalidomide is a standard therapeutic agent for multiple myeloma and clinical trials have been conducted on diseases including a T-cell lymphoma for the purpose of expanding indications (Non-patent literature 3). Lenalidomide is a so-called immunomodulating agent having immunostimulatory activity (Non-patent literature 4) and is known to actually enhance an ADCC activity of a therapeutic antibody such as anti-CD20 antibody and anti-CD40 antibody (Non-patent literatures 5 and 6).

CITATION LIST

Patent Literature
Patent Literature 1: WO01/64754
Patent Literature 2: WO03/18635
Patent Literature 3: WO2005/057341
Non-Patent Literature
Non-patent Literature 1: *Clinical Cancer Research*, vol. 9, p 3625, 2003
Non-patent Literature 2: *J Invest Dermatol*, vol. 119, p 1405, 2002
Non-patent Literature 3: *Clin Lymphoma Myeloma. Suppl*, 5, S187, 2008
Non-patent Literature 4: *J Clin Oncol*, vol. 26, p 1544, 2008
Non-patent Literature 5: *Clin Cancer Res*, vol. 11, p 5984, 2005
Non-patent Literature 6: *Br J Haematol.*, vol. 144, p 848, 2009

SUMMARY OF THE INVENTION

An object of the present invention is to provide a pharmaceutical composition comprising a recombinant antibody against CCR4 and at least one medicament; and a pharmaceutical composition for administering a recombinant antibody against CCR4 and at least one medicament in combination. However, any combination therapy of Lenalidomide and a therapeutic antibody has not been approved in clinical practice. In addition, there is no report about combination effect of an anti-CCR4 antibody and Lenalidomide on T-cell lymphoma.

The present invention can provide a pharmaceutical composition comprising a recombinant antibody against CCR4 and at least one medicament; and a pharmaceutical composition for administering a recombinant antibody against CCR4 and at least one medicament in combination.

BRIEF DESCRIPTION OF THE DRAWINGS

FIG. 1 shows combination effect of an anti-CCR4 antibody and Lenalidomide on HH cells grafted into SCID mice. The ordinate shows a V/V0 value. The abscissa shows the number of days. ●, □, ▲ and x indicate the average V/V0 values of a negative control group, a group administering KM8760 alone, a group administering Lenalidomide alone, and a group administering KM8760 and Lenalidomide in combination, respectively.

FIG. 2 shows combination effect of an anti-CCR4 antibody and Lenalidomide on HH cells grafted into SCID mice. The ordinate shows a V/V0 value. The abscissa shows the number of days after the start of administration. ○, ▲, ■, and x indicate the average V/V0 values of a negative control group (administration of medium), a group administering KM8760 alone, a group administering Lenalidomide alone, and a group administering KM8760 and Lenalidomide in combination, respectively.

FIG. 3A shows ADCC activity of KM8760 when hPBMCs and HH cells were used as effector cells and target cells, respectively. The ordinate shows the cytotoxicity rate (Lysis %) and the abscissa shows the antibody concentration (μmol/L). ○, ●, Δ and ■ indicate the average cytotoxicity rate (the sample number N=3), which were measured using the effector cells treated with no Lenalidomide and 0.1 μmol/L, 1 μmol/L and 10 μmol/L of Lenalidomide, respectively, for one day.

FIG. 3B shows ADCC activity of KM8760 when hPBMCs and HH cells were used as effector cells and target cells, respectively. The ordinate shows the cytotoxicity rate (Lysis %) and the abscissa shows the antibody concentration (μmol/L). ○, ●, Δ and ■ indicate the average cytotoxicity rate (the sample number N=3), which were measured using the effector cells treated with no Lenalidomide and 0.1 μmol/L, 1 μmol/L and 10 μmol/L of Lenalidomide, respectively, for three days.

FIG. 3C shows ADCC activity of KM8760 when hPBMCs and HH cells were used as effector cells and target cells, respectively. The ordinate shows the cytotoxicity rate (Lysis %) and the abscissa shows the antibody concentration (μmol/L). ○, ●, Δ and ■ indicate the average cytotoxicity rate (the sample number N=3), which were measured using the effector cells treated with no Lenalidomide and 0.1 μmol/L, 1 μmol/L and 10 μmol/L of Lenalidomide, respectively, for five days.

DETAILED DESCRIPTION OF THE INVENTION

Figure 1:
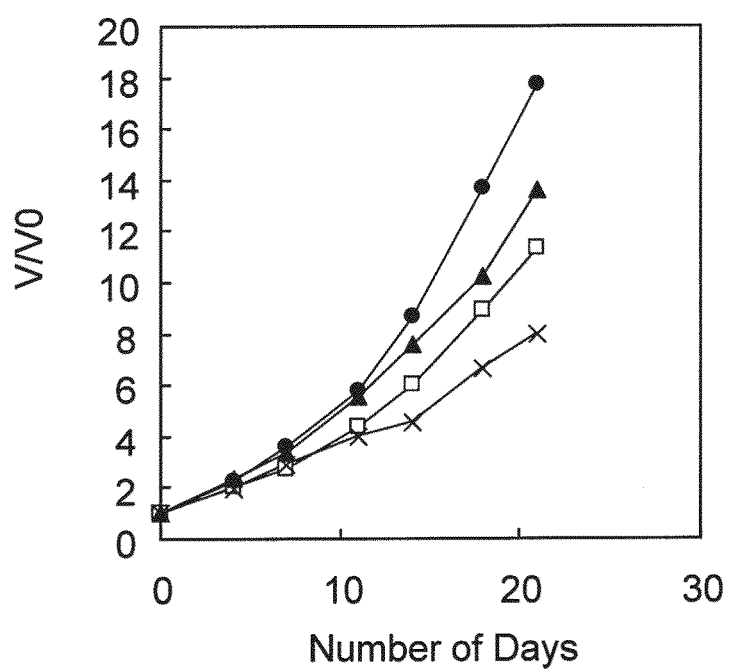
[FIG. 1]

Namely, the present invention relates to the following (1) to (10):

(1) A pharmaceutical composition, comprising an antibody composition which specifically binds to human CC chemokine receptor 4 (CCR4) and Lenalidomide;

(2) A pharmaceutical composition for administering a recombinant antibody which specifically binds to CCR4 and Lenalidomide in combination;

(3) The pharmaceutical composition described in the above (2), wherein the pharmaceutical composition for administering in combination is a pharmaceutical composition for simultaneously or sequentially administering;

(4) The pharmaceutical composition described in any one of the above (1) to (3), wherein the pharmaceutical composition is an anti-tumor agent;

(5) The pharmaceutical composition described in the above (4), wherein the tumor is tumor which expresses CCR4;

(6) The pharmaceutical composition described in the above (5), wherein the tumor which expresses CCR4 is T-cell lymphoma;

(7) The pharmaceutical composition described in any one of the above (1) to (6), wherein the recombinant antibody is an antibody having a high antibody-dependent cellular cytotoxicity;

(8) The pharmaceutical composition described in any one of the above (1) to (7), wherein the recombinant antibody is a humanized antibody;

(9) The pharmaceutical composition described in the above (8), wherein the humanized antibody comprises complementarity determining region (hereinafter also referred to as CDR) 1, CDR2 and CDR3 of a heavy chain (hereinafter also referred to as H chain) variable region (hereinafter also referred to as V region) of an antibody molecule comprising the amino acid sequences represented by SEQ ID NOs: 5, 6 and 7, respectively, and CDR1, CDR2 and CDR3 of a light chain (hereinafter also referred to as L chain) V region of an antibody comprising the amino acid sequences represented by SEQ ID NOs:8, 9 and 10, respectively; and

(10) The pharmaceutical composition described in the above (9), wherein, in the humanized antibody, the H chain V region of an antibody molecule comprises the amino acid sequences represented by SEQ ID NO:11, and the L chain V region of an antibody molecule comprises the amino acid sequences represented by SEQ ID NO:12.

Examples of the pharmaceutical composition of the present invention include a pharmaceutical composition comprising a recombinant antibody against CCR4 and at least one medicament; and a pharmaceutical composition for administering a recombinant antibody against CCR4 and at least one medicament in combination.

Herein, the pharmaceutical composition comprising a recombinant antibody against CCR4 and at least one medicament may be a combination drug in which each medicament component is mixed, or a pharmaceutical composition for simultaneously or sequentially administering a recombinant antibody which specifically binds to CCR4 and at least one medicament in combination after preparing each medicament separately. Examples of the combination drug in which each medicament component is mixed include a fusion antibody in which at least one medicament is bound to a recombinant antibody which specifically binds to CCR4 and the like.

The pharmaceutical composition for administering a recombinant antibody against CCR4 and at least one medicament in combination may be a pharmaceutical composition for simultaneously or sequentially administering a recombinant antibody which specifically binds to CCR4 and at least one medicament in combination after preparing each medicament separately, or a combination drug in which each medicament component is mixed. Examples of the combination drug in which each medicament component is mixed include a fusion antibody in which at least one medicament is bound to a recombinant antibody which specifically binds to CCR4 and the like.

In addition, these medicaments may be simultaneously or sequentially administered to a patient after adjusting a pharmaceutical kit comprising each medicament, or administered after mixing these medicaments.

When a recombinant antibody which specifically reacts to CCR4 and at least one medicament are simultaneously administered, the order of administration is not limited. The recombinant antibody which specifically binds to CCR4 may be administered to a patient before or after administering at least one medicament. The term "sequentially" means that a recombinant antibody and at least one medicament are administered in one after another within a time frame so that these medicaments can therapeutically act within the same time frame.

In the present invention, examples of the recombinant antibody which specifically binds to CCR4 include a recombinant antibody which specifically reacts with an extracellular region of human CCR4. Among them, a recombinant antibody which does not show reactivity with a human blood platelet, a recombinant antibody having high antibody-dependent cellular cytotoxicity (hereinafter also referred to as ADCC activity) and the like are preferable.

What an antibody does not show reactivity with a human blood platelet as referred to here means that an antibody does not substantially react with a human blood platelet. Specifically, it means that reactivity is not shown by the measurement with a flow cytometer.

Also, the antibody in the present invention includes an antibody which specifically reacts with preferably the region comprising positions 1 to 39, 98 to 112, 176 to 206 or 271 to 284 in the amino acid sequence represented by SEQ ID NO:1, more preferably the region comprising positions 2 to 29 (SEQ ID NO:2) in the amino acid sequence represented by SEQ ID NO:1, still more preferably the region comprising positions 12 to 29 (SEQ ID NO:3) in the amino acid sequence represented by SEQ ID NO:1, and particularly preferably the region comprising positions 13 to 25 (SEQ ID NO:4) in the amino acid sequence represented by SEQ ID NO:1. In addition, examples also include an antibody which specifically reacts to an epitope which is recognized by a monoclonal antibody binding to CCR4 which is produced by a hybridoma KM2160 (FERM BP-10090) disclosed in WO2005/053741 and the like.

In addition, the antibody in the present invention include an antibody which is produced by cells resistant to a lectin which recognizes a sugar chain structure in which 1-position of fucose is bound to 6-position of N-acetylglucosamine in the reducing end through α-bond in a complex type N-glycoside-linked sugar chain (WO02/31140, WO03/58118 and WO03/85107).

Examples of the recombinant antibody in the present invention include a humanized antibody, a human antibody and the like.

Examples of the humanized antibody include a human chimeric antibody, a human CDR-grafted antibody and the like.

The human chimeric antibody refers an antibody comprising H chain V region (hereinafter also referred to as HV or VH) of an antibody of a non-human animal, and L chain V region (hereinafter also referred to as LV or VL) of an antibody of a non-human animal, and H chain C region (hereinafter referred to as CH) of a human antibody and L chain C region (hereinafter referred to as CL) of a human antibody. As the non-human animals, any animal, such as a mouse, a rat, a hamster and a rabbit, can be used so long as a hybridoma cell can be prepared from the animal.

The human chimeric antibody of the present invention can be produced by obtaining cDNAs encoding VH and VL of an antibody from a non-human animal hybridoma capable of producing a monoclonal antibody derived from non-human animal which specifically binds to CCR4, inserting them into an expression vector for animal cell having genes encoding human antibody CH and human antibody CL to thereby construct a vector for expression of human chimeric antibody, and then introducing the vector into a host cell to express the antibody.

Any CH of a human chimeric antibody can be used, so long as it belongs to human immmogloblin (hereinafter referred to as hIg), but those of the hIgG class are preferred, and any one of the subclasses belonging to the IgG such as γ1, γ2, γ3 and γ4 can be also used. Also, as CL of a human chmeric antibody, those of κ class or λ class can be used.

Examples of the human chimeric antibody of the present invention include a human chimeric antibody which comprises CDR1, CDR2 and CDR3 of VH comprising the amino acid sequences represented by SEQ ID NOs:5, 6 and 7, respectively, and CDR1, CDR2 and CDR3 of VL comprising the amino acid sequences represented by SEQ ID NOs:8, 9 and 10, respectively. More specifically, examples include a human chimeric antibody in which the amino acid sequences of VH and VL are the amino acid sequences represented by SEQ ID NOs:11 and 12, respectively.

Specific examples include a human chimeric antibody in which VH comprises the amino acid sequence represented by SEQ ID NO:11, CH comprises the amino acid sequence of the IgG1 subclass of a human antibody, VL comprises the amino acid sequence represented by SEQ ID NO:12 and CL comprises the amino acid sequence of class of a human antibody. Examples include anti-CCR4 human chimeric antibody KM2760 disclosed in WO01/64754 and the like.

A human CDR-grafted antibody refers to an antibody in which amino acid sequences of CDRs of VH and VL of an antibody derived from a non-human animal are grafted into appropriate sites in VH and VL of a human antibody.

The human CDR-grafted antibody of the present invention can be produced by constructing cDNAs encoding V regions in which amino acid sequences of CDRs of VH and VL of an antibody derived from a non-human animal which specifically binds to CCR4 are grafted into frameworks (hereinafter referred to as "FR") of VH and VL of an arbitrary human antibody, inserting the resulting cDNAs into an expression vector for animal cells which have DNAs encoding CH and CL of a human antibody, respectively, to construct a human CDR-grafted antibody expression vector, and introducing the expression vector into an animal cell to induce expression.

As a method for selecting the amino acid sequences of FRs of VH and VL of a human antibody, any of those derived from human antibodies can be used. Examples of the method for selecting include the amino acid sequences of FRs of VH and VL of human antibodies registered in database such as Protein Data Bank, and the amino acid sequences common to each subgroup of FRs of VH and VL of human antibodies (*Sequences of Proteins of Immunological Interest*, US Dept. Health and Human Services, 1991), and the like.

As CH of the antibody of the present invention, any CH can be used, so long as it belongs to hIg and those of the hIgG class are preferred. In addition, any one of the subclasses belonging to the IgG class, such as γ1, γ2, γ3 and γ4 can be used. Also, as CL of the human CDR-grafted antibody, those belonging to the κ class or λ class can be used.

Examples of the human CDR-grafted antibody of the present invention include a human chimeric antibody in which CDR1, CDR2 and CDR3 of VH of the antibody comprise the amino acid sequences represented by SEQ ID NOs: 5, 6 and 7, respectively, and/or CDR1, CDR2 and CDR3 of VL comprise the amino acid sequences represented by SEQ ID NOs:8, 9 and 10, respectively; and the like.

In addition, as the human CDR-grafted antibody of the present invention include a human CDR-grafted antibody wherein VH comprises the amino acid sequence represented by SEQ ID NO:11 and VL comprises the amino acid sequence represented by SEQ ID NO:12 is preferably used.

A human antibody originally means an antibody naturally existing in the human body, and it also includes an antibody obtained from a human antibody phage library or a human antibody-producing transgenic animal, which is prepared based on the recent advanced techniques in genetic engineering, cell engineering and developmental engineering and the like.

With respect to the antibody naturally existing in the human body, human peripheral blood lymphocytes are isolated, infected with EB virus or the like for immortalization and cloning, whereby lymphocytes producing the antibody can be cultured, and the antibody can be purified from the culture.

The human antibody phage library is a library in which antibody gene from a human B cell is inserted into a phage gene to express an antibody fragments such as Fab and scFv on the surface of the phage.

A library in which mutation is artificially introduced can be used to develop the library. A phage having a desired antigen binding activity can be recovered from the library, using a binding activity to a substrate having an antigen-immobilized thereon as an index. The antibody fragment can be further converted to a human antibody molecule comprising two full length H chains and two full length L chains by a protein engineering method.

The human antibody-producing transgenic animal means an animal in which a human antibody gene is incorporated into cells. Examples of the human antibody-producing transgenic animal include a human antibody-producing transgenic mouse which is prepared by introducing a human antibody gene into a mouse ES cell, grafting the ES cell on an early embryo of the mouse and developing the same, and the like.

Regarding a method for preparing a human antibody from the human antibody-producing transgenic animal, the human antibody can be produced and accumulated in a culture supernatant by culturing a human antibody-producing hybridoma obtained by a hybridoma preparation method using a general cell fusion method.

Examples of the transgenic non-human animals include cattle, sheep, goats, pigs, horses, mice, rats, chickens, monkeys, rabbits and the like.

Herein, examples of a recombinant antibody having a high ADCC activity include a composition comprising an antibody molecule having a complex type N-glycoside-linked sugar chain in the Fc region, and comprising a sugar chain in which fucose is not bound to N-acetylglucosamine in the reducing end in the sugar chain among the total complex N-glycoside-linked sugar chains binding to the Fc region in the antibody composition reducing end.

In the present specification, a high antibody-dependent cellular cytotoxicity means that the antibody has a higher ADCC activity than those mainly produced in a living body.

In addition, in the preset invention, an antibody having a high ADCC activity is hereinafter referred to as an antibody lacking in fucose modification.

Specific examples include a human CDR-grafted antibody which is an antibody lacking in fucose modification which specifically binds to CCR4 and comprises VH comprising the amino acid sequence represented by SEQ ID NO:11 and VL comprising the amino acid sequence represented by SEQ ID NO:12 (hereinafter also referred to as KM8760).

An N-glycoside-linked sugar chain is bound to the Fc region in an antibody molecule. Therefore, two sugar chains are bound to one antibody molecule.

Examples of the N-glycoside-linked sugar chain include a complex type sugar chain in which the non-reducing end side of the core structure has one or more parallel branches containing galactose-N-acetylglucosamine (hereinafter referred to as "Gal-GlcNAc") and the non-reducing end side of Gal-GlcNAc has sialic acid, bisecting N-acetylglucosamine and the like.

In the present invention, the N-glycoside-linked sugar chain is shown by the following formula.

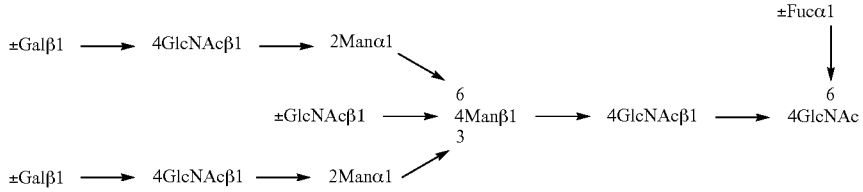

In the present invention, a gene antibody which specifically binds to CCR4 may be administered as a composition. Among the gene antibody compositions which specifically bind to CCR4, the recombinant antibody composition comprising an antibody molecule the N-glycoside-linked sugar chain in the Fc region may be comprised of an antibody molecule having a single sugar chain structure or an antibody molecule having plural and different sugar chain structures, so long as it has the above sugar chain structure. That is, the recombinant antibody composition of the present invention means a composition comprising a recombinant antibody molecule having a single or plural and different sugar chain structure(s).

As the ratio of sugar chains in which fucose is not bound to N-acetylglucosamine in the reducing end of the antibody, antibodies having any ratio are included, so long as the ADCC activity is increased. The ratio is preferably 20% or more, more preferably 51% to 100%, still more preferably 80% to 100%, particularly preferably 90% to 99% and most preferably 100%.

In the present invention, the sugar chain in which fucose is not bound may have any sugar chain structure in the non-reducing end, so long as fucose is not bound to N-acetylglucosamine in the reducing end in the above formula.

In the present invention, the case where fucose is not bound to N-acetylglucosamine in the reducing end in the sugar chain means that fucose is not substantially bound. An antibody composition in which fucose is not substantially bound specifically refers to an antibody composition in such a degree that fucose is not substantially detected according to the known sugar chain analysis (WO02/31140, WO03/85107).

The degree that fucose is not substantially detected means the content of fucose is below the detection limit. A recombinant antibody composition in which fucose is not bound to N-acetylglucosamine in the reducing ends of all sugar chains has the highest ADCC activity.

The ratio of sugar chains in which fucose is not bound to N-acetylglucosamine in the reducing end in the sugar chains contained in the composition which comprises an antibody molecule having complex type N-glycoside-linked sugar chains in the Fc region can be determined by the following analytic methods.

Examples of the analytic method include a method in which the sugar chains are released from the antibody molecule using a known method such as hydrazinolysis or enzyme digestion [*Biochemical Experimentation Methods 23—Method for Studying Glycoprotein Sugar Chain* (Japan Scientific Societies Press), edited by Reiko Takahashi (1989)], the released sugar chain was subject to fluorescence labeling or radioisotope labeling and then the labeled sugar chains by chromatography were separated. Also, the released sugar chains can also be analyzed using the HPAED-PAD method [*J. Liq. Chromatogr.*, 6, 1577 (1983)].

The transformant producing the recombinant antibody composition which specifically binds to CCR4 of the present invention can be obtained by introducing, into an animal cell, a recombinant antibody composition expression vector into which DNAs encoding a variable region and a constant region of an antibody molecule are inserted.

The recombinant antibody composition expression vector can be constructed as described below (WO02/31140, WO03/85107).

Each of the above DNAs encoding CH and CL is introduced into an expression vector in animal cell to produce an expression vector for animal cell.

The expression vector for animal cell includes pAGE107 (Japanese Published Unexamined Patent Application No. 22979/91; Miyaji H. et al., *Cytotechnology*, 3, 133-140 (1990)), pAGE103 (Mizukami T. and Itoh S., *J. Biochem.*, 101, 1307-1310 (1987)), pHSG274 (Brady G. et al., *Gene*, 27, 223-232 (1984)), pKCR (O'Hare K. et al., *Proc. Natl. Acad. Sci. USA.*, 78, 1527-1531 (1981)), pSG1βd2-4 (Miyaji H. et al., *Cytotechnology*, 4, 173-180 (1990)) and the like. The promoter and enhancer used for the expression vector for animal cell include SV40 early promoter and enhancer (Mizukami T. and Itoh S., *J. Biochem.*, 101, 1307-1310 (1987)), LTR promoter and enhancer of Moloney mouse leukemia virus (Kuwana Y. et al., *Biochem. Biophys. Res. Commun.*, 149, 960-968 (1987)), immunoglobulin H chain promoter (Mason J. O. et al., *Cell*, 41, 479-487 (1985)) and ehnancer (Gillies S. D. et al., *Cell*, 33, 717-728 (1983)) and the like.

The vector for expression of recombinant antibody composition may be either of a type in which genes encoding the H chain and L chain exist on separate vectors or of a type in which both genes exist on the same vector (tandem type). In respect of easiness of construction of a recombinant antibody composition expression vector, easiness of introduction into animal cells, and balance between the expression amounts of the H and L chains of an antibody in animal cells, a tandem type of the vector for expression of recombinant antibody composition is more preferred (Shitara K. et al., *J. Immunol. Methods*, 167, 271-278 (1994)). The tandem type vector for expression of recombinant antibody composition includes pKANTEX93 (WO97/10354), pEE18 (Bentley K. J. et al., Hybridoma, 17, 559-567 (1998)) and the like.

cDNAs encoding VH and VL of antibodies for various antigens are cloned into the upstream of DNAs encoding CH and CL of the constructed vector for expression of a recombinant antibody composition to thereby construct a recombinant antibody composition expression vector.

A method for introducing the expression vector into a host cell includes electroporation (Japanese Published Unexamined Patent Application No. 257891/90; Miyaji H. et al., *Cytotechnology*, 3, 133-140 (1990)) and the like.

The host cell producing the recombinant antibody composition of the present invention may be any host cell which is generally used in production of a recombinant protein, such as an animal cell, a plant cell or a microorganism.

The host cell producing the recombinant antibody composition of the present invention includes a CHO cell derived from a Chinese hamster ovary tissue, a rat myeloma cell line YB2/3HL.P2.G11.16Ag.20 cell, a mouse myeloma cell line NS0 cell, a mouse myeloma SP2/0-Ag 14 cell, a BHK cell derived from a Syrian hamster kidney tissue, a human leukemia cell line Namalwa cell, a hybridoma cell produced by using a myeloma cell and any B cell, a hybridoma cell produced by a B cell obtained by immunizing with an antigen a transgenic non-human animal produced by using an embryonic stem cell or a fertilized egg cell and any myeloma cell; a hybridoma cell produced by the above myeloma cell and a B cell obtained by immunizing a transgenic non-human animal produced by using an embryonic stem cell or a fertilized egg cell; and the like, with an antigen.

The host cell capable of expressing a recombinant antibody composition having a high ADCC activity includes a host cell resistant to a lectin which recognizes a sugar chain structure in which 1-position of fucose is bound to 6-position of N-acetylglucosamine in the reducing end through α-bond in the complex type N-glycoside-linked sugar chain, such as a host cell capable of producing an antibody composition comprising an antibody molecule having complex type N-glycoside-linked sugar chains in the Fc region, wherein the ratio of sugar chains in which fucose is not bound to N-acetylglucosamine in the reducing end of the sugar chains among the total complex type N-glycoside-linked sugar chains which bind to the Fc region contained in the composition is 20% or more. Examples include cells in which activity of at least one protein described below is decreased or deleted, such as the following (a) to (c):

(a) an enzyme relating to synthesis of an intracellular sugar nucleotide, GDP-fucose;
(b) an enzyme relating to modification of a sugar chain in which 1-position of fucose is bound to 6-position of N-acetylglucosamine in the reducing end through α-bond in a complex type N-glycoside-linked sugar chain;
(c) a protein relating to transport of an intracellular sugar nucleotide, GDP-fucose, to the Golgi body (WO02/31140, WO03/85107), and the like.

The above host cell is preferably a host cell in which a gene encoding α1,6-fucosyltransferase in the host cell is knocked out (WO02/31140, WO03/85107).

The enzyme relating to synthesis of an intracellular sugar nucleotide, GDP-fucose may be any enzyme, so long as it is an enzyme relating to the synthesis of the intracellular sugar nucleotide, GDP-fucose, as a supply source of fucose to a sugar chain.

The enzyme relating to synthesis of an intracellular sugar nucleotide, GDP-fucose includes an enzyme which has influence on the synthesis of the intracellular sugar nucleotide, GDP-fucose, and the like.

The intracellular sugar nucleotide, GDP-fucose, is supplied by a de novo synthesis pathway or a salvage synthesis pathway. Thus, all enzymes relating to the synthesis pathways are included in the enzyme relating to synthesis of an intracellular sugar nucleotide, GDP-fucose.

The enzyme relating to the de novo synthesis pathway of an intracellular sugar nucleotide, GDP-fucose includes GDP-mannose 4,6-dehydratase (hereinafter referred to as "GMD"), GDP-keto-6-deoxymannose-3,5-epimerase, 4,6-reductase (hereinafter referred to as "Fx") and the like.

The enzyme relating to the salvage synthesis pathway of an intracellular sugar nucleotide, GDP-fucose includes GDP-beta-L-fucose pyrophosphorylase (hereinafter referred to as "GFPP"), fucokinase and the like.

As the enzyme which has influence on the synthesis of an intracellular sugar nucleotide, GDP-fucose, an enzyme which has influence on the activity of the enzyme relating to the synthesis pathway of the intracellular sugar nucleotide, GDP-fucose described above, and an enzyme which has influence on the structure of substances as the substrate of the enzyme are also included.

The enzyme relating to modification of a sugar chain in which 1-position of fucose is bound to 6-position of N-acetylglucosamine in the reducing end through α-bond in a complex type N-glycoside-linked sugar chain includes any enzyme, so long as it is an enzyme relating to the reaction of binding of 1-position of fucose to 6-position of N-acetylglucosamine in the reducing end through α-bond in the complex type N-glycoside-linked sugar chain.

The enzyme relating to the reaction of binding of 1-position of fucose to 6-position of N-acetylglucosamine in the reducing end through α-bond in the complex type N-glycoside-linked sugar chain includes an enzyme which has influence on the reaction of binding of 1-position of fucose to 6-position of N-acetylglucosamine in the reducing end through α-bond in the complex type N-glycoside-linked sugar chain. Examples include α1,6-fucosyltransferase, α-L-fucosidase and the like.

Also, the enzyme relating to the reaction of binding of 1-position of fucose to 6-position of N-acetylglucosamine in the reducing end through α-bond in the complex type N-glycoside-linked sugar chain includes an enzyme which has influence on the activity of the enzyme relating to the reaction of binding of 1-position of fucose to 6-position of N-acetylglucosamine in the reducing end through α-bond in the complex type N-glycoside-linked sugar chain and an enzyme which has influence on the structure of substances as the substrate of the enzyme.

The protein relating to transport of an intracellular sugar nucleotide, GDP-fucose, to the Golgi body may be any protein, so long as it is a protein relating to the transport of the intracellular sugar nucleotide, GDP-fucose, to the Golgi body, or a protein which has an influence on the reaction for the transport of the intracellular sugar nucleotide, GDP-fucose, to the Golgi body.

The protein relating to the transport of the intracellular sugar nucleotide, GDP-fucose, to the Golgi body includes a GDP-fucose transporter and the like.

Also, the protein which has an influence on the reaction for the transport of the intracellular sugar nucleotide, GDP-fucose, to the Golgi body include a protein which has an influence on the activity of the above protein relating to the transport of the intracellular sugar nucleotide, GDP-fucose, to the Golgi body or has influence on the expression thereof.

The method for obtaining a cell in which the above enzyme activity is decreased or deleted may by any method, so long as it is a method for decreasing or deleting the objective enzyme activity. Examples include the following (a) to (e):

(a) a gene disrupting technique targeting a gene encoding the enzyme;
(b) a technique for introducing a dominant-negative mutant of a gene encoding the enzyme;
(c) a technique for introducing mutation into the enzyme;

(d) a technique for inhibiting transcription or translation of a gene encoding the enzyme;
(e) a technique for selecting a cell line resistant to a lectin which recognizes a sugar chain structure in which 1-position of fucose is bound to 6-position of N-acetylglucosamine in the reducing end through α-bond in a N-glycoside-linked sugar chain;
and the like (WO02/31140, WO03/85107).

As the lectin which recognizes a sugar chain structure in which 1-position of fucose is bound to 6-position of N-acetyl-glucosamine in the reducing end through α-bond in a N-glycoside-linked sugar chain, any lectin capable of recognizing the sugar chain structure can be used. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*), *Aleuria aurantia* lectin AAL (lectin derived from *Aleuria aurantia*) and the like.

The cell resistant to a lectin refers to a cell in which growth is not inhibited by the presence of a lectin at an effective concentration. The effective concentration is a concentration higher than the concentration that does not allow the normal growth of a cell prior to the genome modification (hereinafter referred to also as parent cell line). The effective concentration is preferably equal to the concentration that does not allow the normal growth of a cell prior to the genome modification, more preferably 2 to 5 times, further preferably 10 times, most preferably 20 or more times the concentration that does not allow the normal growth of a cell prior to the modification of the genomic gene.

The effective concentration of lectin that does not inhibit growth may be appropriately determined according to each cell line. It is usually 10 μg/ml to 10 mg/ml, preferably 0.5 mg/ml to 2.0 mg/ml.

In the pharmaceutical composition in the present invention, examples of at least one medicament include an immunomodulating agent, such as Lenalidomide and Actimid.

There is concern that the above medicament may produce adverse effects in the case where the medicament is administered alone to a living body at a high dose. However, in the present invention, the above medicament can be administered at a low dose by combining the above medicament with a recombinant antibody which specifically binds to CCR4.

Therefore, use of the above medicament and the antibody in combination can reduce adverse effect as well as exhibit sufficient therapeutic effect. In addition, pathological condition is rare to cure only by the above medicament and many of patients experience a relapse. In the present invention, higher therapeutic effect can be expected by combining the above medicament with a recombinant antibody which specifically binds to CCR4.

The pharmaceutical composition of the present invention can be combined with the following other medicaments or methods.

Examples of the above medicaments or methods include drugs for multidrug chemotherapy, such as CHOP therapy which combines cyclophosphamide, doxorubicin, vincristine, and prednisolone; CHOP-like therapy, such as THP-COP therapy which combines pirarubicin instead of doxorubicin; EPOCH therapy which adds etoposide to CHOP therapy; ESHAP therapy which combines etoposide, cisplatin, methylprednisolone, and cytarabine; LSG15 therapy which combines vincristine, cyclophosphamide, doxorubicin, prednisolone, ranimustine, vindesine, etoposide, and carboplatin; modified LSG 15 therapy (also referred to as mLSG15 therapy) which combines vincristine, cyclophosphamide, doxorubicin, prednisolone, ranimustine, vindesine etoposide, carboplatin, cytarabine, and methotrexate; ABVD therapy which combines doxorubicin, bleomycin, vinblastine, and dacarbazine; and the like, and molecular targeting drugs.

Examples for the molecular targeting drugs include a nucleotide analogue, a monoclonal antibody, a histone deacetylase inhibitor (HDAC inhibitor), a folic acid analog, a signal inhibitor and proteasome inhibitor and the like.

Examples of the folic acid analogs include Gemcitabine, Cladribine, Fludarabine, Pentostatin, Forodesine, Pralatrexate and the like.

Examples of the monoclonal antibodies include Alemtuzumab, Bevacizumab, SGN-30, Iratumumab, Zanolimumab, Siplizumab, Denileukin diftitox and the like.

Examples of the HDAC inhibitors include Vorinostat, Belinostat, Panobinostat, Romidepsin and the like.

Examples of the signal inhibitors include Enzastaurin and the like.

Examples of the proteasome inhibitors include Bortezomib and the like.

In the pharmaceutical composition of the present invention, examples of at least one medicament include Gemcitabine, Cladribine, Fludarabine, Pentostatin, Forodesine, Alemtuzumab, Bevacizumab, SGN-30, Iratumumab, Zanolimumab, Sevirumab, Denileukin diftitox, Vorinostat, Belinostat, Panobinostat, Romidepsin, Pralatrexate, Enzasutaurin and Bortezomib, and the combination of these medicaments.

The pharmaceutical composition of the present invention can be applied to any tumor which expresses CCR4 regardless of the type of the cancer. Examples of the tumor include hematopoietic organ tumor.

Examples of hematopoietic organ tumor include acute leukemia, chronic leukemia, non-Hodgkin's disease, Hodgkin's disease (or Hodgkin's lymphoma) and the like.

Examples of the acute leukemia include acute lymphatic leukemia and the like.

Examples of the chronic leukemia include chronic lymphatic leukemia and the like.

Examples of the non-Hodgkin's disease include precursor T lymphoblastic leukemia/lymphoma, mature T cell tumor, NK cell tumor and the like.

Examples of mature T cell tumor and NK cell tumor include T cell prolymphocytic leukemia, T cell large granular lymphocytic leukemia, Sezary syndrome, NK leukemia cells of extranodal NK/T cell lymphoma (nasal type), mycosis fungoides, primary cutaneous anaplastic large cell lymphoma, subcutaneous panniculitis-like T-cell lymphoma, enteropathy-type T-cell lymphoma, hepatosplenic γδT-cell lymphoma, angioimmunoblastic T-cell lymphoma, peripheral T-cell lymphoma (non-specific), anaplastic large cell lymphoma (ALK positive, ALK negative), and adult T-cell leukemia/lymphoma and the like.

Examples of Hodgkin's lymphoma include nodular lymphocyte predominant Hodgkin lymphoma, classical Hodgkin lymphoma and the like. Examples of classical Hodgkin lymphoma include nodular sclerosis Hodgkin's lymphoma, lymphocyte-rich classical Hodgkin's lymphoma, mixed cellularity Hodgkin's lymphoma, lymphocytic depleted Hodgkin's lymphoma and the like.

Examples of the therapy which can be conducted in combination with the administration of the pharmaceutical composition of the present invention include surgery, blood transfusions, immunotherapy, biologic therapy, radiation therapy and other non-drug therapies. However, examples are not limited to the above.

The effect of the pharmaceutical composition of the present invention may be examined by measuring an in vivo antitumor activity using animal models.

Examples of the animal models include xenograft models obtained by transplanting a culture cell line derived from a human cancer tissue into mice. The xenograft models can be obtained by transplanting a human cancer cell line into various regions of immunodeficient mice, such as SCID mice, for example, subcutaneousely, intracutaneously, intraperitoneally, or intravenously.

The effect of the pharmaceutical composition of the present invention can be evaluated by comparing an effect of administration of the antibody alone or an effect of administration of the agent alone with an effect of the pharmaceutical composition of the present invention by using the above animal models.

The pharmaceutical composition of the present invention may be administered alone as a therapeutic agent. However, it is preferably mixed with one or more pharmaceutically acceptable carriers and then provided as a pharmaceutical preparation produced by any method well known in the technical field of pharmaceutical preparations.

It is preferable to administer the pharmaceutical composition by the route that is most effective for the treatment. Suitable administration routes include oral administration and parenteral administration such as intraoral administration, intratracheal administration, intrarectal administration, subcutaneous administration, intramuscular administration and intravenous administration. In the case of a protein preparation, intravenous administration is preferable.

Examples of the preparations for the administration include spray, capsules, tablets, granules, syrup, emulsion, suppository, injection, ointment, tape and the like.

Examples of the preparations suitable for the oral administration include emulsions, syrups, capsules, tablets, powders, granules and the like.

Liquid preparations such as emulsions and syrups can be prepared using, as additives, water, sugars such as sucrose, sorbitol and fructose, glycols such as polyethylene glycol and propylene glycol, oils such as sesame oil, olive oil and soybean oil, antiseptics such as p-hydroxybenzoates, flavors such as strawberry flavor and peppermint, and the like.

Capsules, tablets, powders, granules, and the like can be prepared using, as additives, excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, and the like.

Examples of the pharmaceutical preparations suitable for parenteral administration include injections, suppositories, sprays and the like.

Injections can be prepared, for example, using carriers comprising a salt solution, a glucose solution, or a mixture thereof, etc.

Suppositories can be prepared, for example, using carriers such as cacao butter, hydrogenated fat and carboxylic acid.

Sprays can be prepared using carriers which do not stimulate the oral or airway mucous membrane of a recipient and which can disperse the pharmaceutical composition as fine particles to facilitate absorption thereof.

Specific examples of the carriers include lactose, glycerin and the like. It is also possible to prepare aerosols, dry powders, and the like according to the properties of the composition and the carriers used. In preparing these parenteral preparations, the above-mentioned additives for the oral preparations may also be added.

A dose or an administration frequency varies depending on the desired therapeutic effect, the administration route, the period of treatment, age, body weight, and the like. However, it is preferable that a dose of the antibody for an adult is generally 0.01 to 5 mg/kg per dose. It is preferable that the medicament administered with the antibody is the same or less than that administered alone in clinical practice in combination.

Industrial Applicability

The present invention can provide a pharmaceutical composition comprising a recombinant antibody against CCR4 and at least one medicament; and a pharmaceutical composition for administering in combination of a recombinant antibody against CCR4 and at least one medicament.

EXAMPLE 1

Antitumor Effect Provided by Administering Anti-CCR4 Antibody and Lenalidomide in Combination (1)

HH cells (cutaneous T cell lymphoma cell line; ATCC No: CRL-2105) were suspended in Dulbecco's phosphate buffered saline without calcium chloride and magnesium chloride (PBS, manufactured by Invitrogen) at a density of $1 \times 1^7$ cells/mL, and 100 µL of the suspension was transplanted into the ventral skin of SCID mouse (obtained by Nippon Crea, male). Seven days after the cell transplantation, a diameter of a tumor was measured with calipers, and a tumor volume was calculated using the following formula.

$$\text{Tumor volume} = \text{short diameter} \times \text{short diameter} \times \text{long diameter} \times 0.5 \quad \text{(Formula)}$$

Individuals having the tumor volume within the range of 41 to 93 mm$^3$ were selected, and grouped such that the average of tumor volume was to be equal. Then, the following administration groups A to D were arranged. The day of grouping was defined as Day 0.

A. Negative control group: Administration of medium
B. Group administering KM8760 alone: 20 mg/kg was administered on Day 0, Day 7 and Day 14.
C. Group administering Lenalidomide alone: 1 mg/kg was administered everyday on Day 0 to Day 13.
D. Group administering KM8760 and Lenalidomide in combination: the respective agent was administered on the same schedule and at the same dose as each group administering respective agent alone.

The experiment was conducted with groups each consisting of eight mice. KM8760 was diluted with saline (manufactured by Otsuka Pharmaceutical), and the obtained solution was administered from the tail vein. Lenalidomide was suspended with saline containing 0.5% of methylcellulose and the obtained solution was intraperitoneally administered. The tumor volume was measured chronologically. The antitumor effect was evaluated by comparing the average values of values (V/V0) obtained by dividing the tumor volume on each day of measurement by the tumor volume on Day 0 in each group.

The chronological change in the average values of V/V0 in each group is shown in FIG. 1. As shown in FIG. 1, the administration of KM8760 and Lenalidomide in combination exhibited higher effect in suppressing growth than the administration of Lenalidomide alone or the antibody alone.

The results of the test for significant differences (One-way ANOVA, Dunnett test) compared with the negative control group are shown in Table 1. In addition, when p<0.05, the value is considered to show a significant difference and is shown with * in the table.

TABLE 1

| | | P value | | | | | |
|---|---|---|---|---|---|---|---|
| | | Day 4 | Day 7 | Day 10 | Day 14 | Day 18 | Day 21 |
| | One-way ANOVA | 0.390 | 0.101 | 0.039* | 0.007* | 0.005* | 0.006* |
| Dunnett | vs KM8760 | 0.751 | 0.071 | 0.119 | 0.070 | 0.034* | 0.046* |
| | vs Lenalidomide | 0.965 | 0.763 | 0.950 | 0.670 | 0.159 | 0.261 |
| | vs Combination administration group | 0.503 | 0.144 | 0.037* | 0.003* | 0.001* | 0.002* |

As shown in Table 1, there was no significant difference between the administration group of the single agent alone and the negative control group on Day 10. However, a significant difference was shown between the combination administration group and the negative control group.

A value (T/C) obtained by dividing V/V0 of each group by V/V0 of the negative control group is shown in Table 2. In the table, * means the case where the actual value of T/C is smaller than the theoretical value.

TABLE 2

| | T/C | | | | | | |
|---|---|---|---|---|---|---|---|
| | Day 0 | Day 4 | Day 7 | Day 10 | Day 14 | Day 17 | Day 21 |
| KM8760 | 1.000 | 0.910 | 0.764 | 0.750 | 0.691 | 0.652 | 0.639 |
| Lenalidomide | 1.000 | 1.041 | 0.918 | 0.948 | 0.875 | 0.750 | 0.766 |
| Combination administration group | | | | | | | |
| (Theoretical value) | 1.000 | 0.948 | 0.701 | 0.712 | 0.604 | 0.489 | 0.489 |
| (Actual value) | 1.000 | 0.870* | 0.800 | 0.684* | 0.520* | 0.487* | 0.450* |

As shown in Table 2, in comparison with a theoretical T/C value which is expected from a simple additive effect of a combination of KM8760 and Lenalidomide, namely, a value obtained by multiplying T/Cs of the groups of administering the respective agent alone, actual T/C of the combined administration group exhibited lower values than the theoretical values on Day 4, Day 10, Day 14, Day 17 and Day 21.

From the above, it has been found that the administration of KM8760 and Lenalidomide in combination has higher antitumor effect than the administration of the respective agent alone.

EXAMPLE 2

Antitumor Effect Provided by Administering Anti-CCR4 Antibody and Lenalidomide in Combination (2)

HH cells (cutaneous T cell lymphoma cell line; ATCC No: CRL-2105) were suspended in Dulbecco's phosphate buffered saline without calcium chloride and magnesium chloride (PBS, manufactured by Invitrogen) at a density of $2 \times 10^8$ cells/mL, and 100 µL of the suspension was transplanted into the ventral skin of SCID mouse (obtained by Nippon Crea, male). Seven days after the cell transplantation, a diameter of a tumor was measured with calipers, and a tumor volume was calculated using the following formula.

Tumor volume=short diameter×short diameter×long diameter×0.5    (Formula)

Individuals having the tumor volume within the range of 51 to 79 mm$^3$ were selected, and grouped such that the average of tumor volume was to be equal. Then, the following administration groups A to D were arranged. The day of grouping was defined as Day 0.

A. Negative control group: Administration of medium

B. Group administering KM8760 alone: 20 mg/kg was administered on Day 0, Day 7, Day 14 and Day 21.

C. Group administering Lenalidomide alone: 1 mg/kg was administered everyday on Day 0 to Day 13.

D. Group administering KM8760 and Lenalidomide in combination: the respective agent was administered on the same schedule and at the same dose as each group administering respective agent alone.

The experiment was conducted with groups each consisting of twelve mice. KM8760 was diluted with saline (manufactured by Otsuka Pharmaceutical), and the obtained solution was administered from the tail vein. Lenalidomide was suspended with saline containing 0.5% of methylcellulose and the diluent was intraperitoneally administered. The tumor volume was measured chronologically. The antitumor effect was evaluated by comparing the average values of values (V/V0) obtained by dividing the tumor volume on each day of measurement by the tumor volume on Day 0 in each group.

Figure 2:
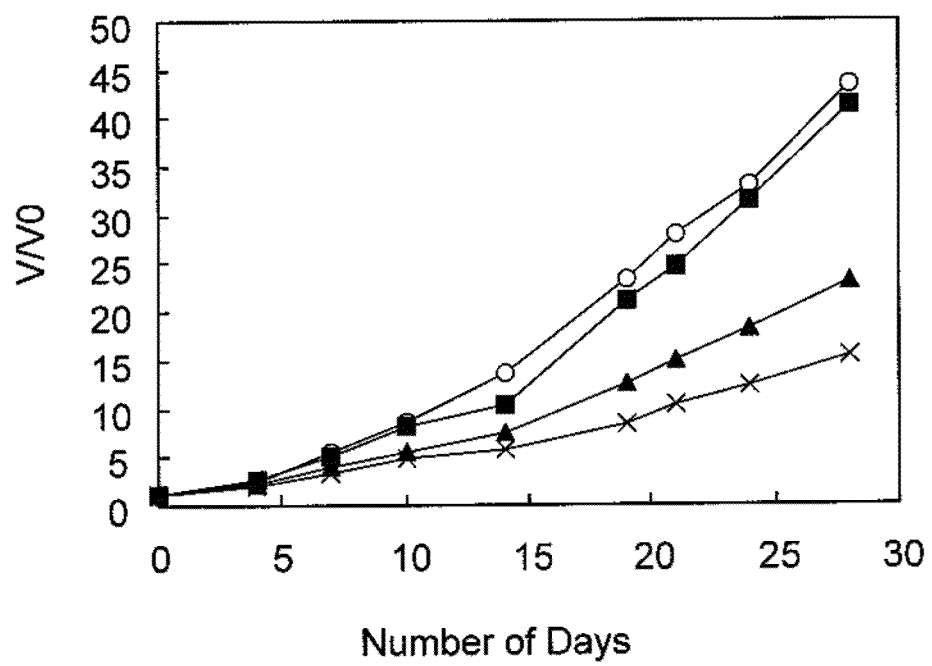
[FIG. 2]

The chronological change in the average values of V/V0 in each group is shown in FIG. 2. As shown in FIG. 2, the administration group of KM8760 and Lenalidomide in combination exhibited higher effect in suppressing growth than the administration group of Lenalidomide alone or the antibody alone.

The result of a test for a significant difference (Steel-Dwass test) between each group administering the respective agent alone and combination administration group is shown in Table 3. In the table, na means not applicable. In addition, when p<0.05, the value is considered to show a significant difference and is shown with * in the table.

TABLE 3

|  | Day 0 | Day 4 | Day 7 | Day 10 | Day 14 | Day 19 | Day 21 | Day 24 | Day 28 |
| --- | --- | --- | --- | --- | --- | --- | --- | --- | --- |
| Kruskal-Wallis test | 1.00 | 0.02 | 0.00 | 0.00 | 0.00 | <0.0001 | 0.00 | 0.00 | 0.00 |
| Steel-Dwass test |  |  |  |  |  |  |  |  |  |
| KM8760 vs Lenalidomide | na | 0.29 | 0.01 | 0.00 | 0.03 | 0.00 | 0.02 | 0.03 | 0.04 |
| KM8760 vs Combination administration group | na | 0.17 | 0.11 | 0.59 | 0.12 | 0.04* | 0.04* | 0.10 | 0.08 |
| Lenalidomide vs Combination administration group | na | 0.02* | 0.00* | 0.00* | 0.00* | 0.00* | 0.00* | 0.00* | 0.00* |

As shown in Table 3, a significant difference was shown between the administration group of Lenalidomide alone and the combination administration group at all points. A significant difference was shown between the administration group of KM8760 alone and the combination administration group on Day 19 and Day 21.

A value (T/C) obtained by dividing V/V0 of each group by V/V0 of the negative control group is shown in Table 4. In the table, * means the case where the actual value of T/C is smaller than the theoretical value.

TABLE 4

| | T/C | | | | | | | | |
| --- | --- | --- | --- | --- | --- | --- | --- | --- | --- |
|  | Day 0 | Day 4 | Day 7 | Day 10 | Day 14 | Day 19 | Day 21 | Day 24 | Day 28 |
| Negative control group | 1.00 | 1.00 | 1.00 | 1.00 | 1.00 | 1.00 | 1.00 | 1.00 | 1.00 |
| KM8760 | 1.00 | 0.89 | 0.71 | 0.62 | 0.54 | 0.54 | 0.54 | 0.55 | 0.53 |
| Lenalidomide | 1.00 | 1.05 | 0.92 | 0.93 | 0.75 | 0.90 | 0.88 | 0.95 | 0.95 |
| Combination administration group |  |  |  |  |  |  |  |  |  |
| (Actual value) | 1.00 | 0.77* | 0.60* | 0.56* | 0.43 | 0.36* | 0.37* | 0.37* | 0.36* |
| (Theoretical value) | 1.00 | 0.94 | 0.66 | 0.58 | 0.41 | 0.49 | 0.47 | 0.52 | 0.50 |

As shown in Table 4, in comparison with a theoretical T/C value which is expected from a simple additive effect of a combination of KM8760 and Lenalidomide, namely, a value obtained by multiplying T/Cs of the groups of administering the respective agents alone, actual T/C of the combined administration group exhibited lower values than the theoretical values on all points except for Day 14.

From the above, it is found that the combination administration of KM8760 and Lenalidomide exhibited higher anti-tumor effect than the respective either agent alone.

EXAMPLE 3

Enhancement of Antibody-Dependent Cellular Cytotoxicity (ADCC) by treating Lenalidomide and Anti-CCR4 antibody in Combination Mononuclear cells (hPBMC) were obtained from peripheral blood from healthy adults by density-gradient centrifugation using Ficoll-paque (manufactured by GE health care). The obtained hPBMC was suspended in RPMI1640 medium containing 10% of FBS and 1% of penicillin/streptomycin solution (manufactured by Nacalai Tesque) (hereinafter referred to as medium). Lenalidomide was added to the suspension to give a final concentration of 0.1, 1 or 10 μmol/L. The obtained suspension was incubated at 37° C. for one, three or five days. Thereafter incubation, hPBMC was washed one time with the medium, and the washed cells were adjusted to give a concentration of about $5 \times 10^6$ cells/mL using the medium. The obtained cells were used as effector cells.

After $1 \times 10^6$ of HH cells suspended in about 100 μl, and 20 μL of $^{51}$Cr solution (NEZ030, manufactured by Perkin-Elmer) were mixed, the mixed solution was incubated at 37° C. for 2 to 4 hours so that HH cells were radiolabeled. After the radiolabeled HH cells were washed three times with the medium, the washed cells were adjusted to give a concentration of about $2 \times 10^5$ cells/mL. The obtained cells were used as target cells.

KM8760 was adjusted to give a concentration of 0.03, 0.3, or 3 μg/mL, using the medium. The obtained solution was used as antibody solution.

On a 96-well U-bottom plate, 50 μL of each of effector cells, target cells and antibody solution was mixed (effector cell: target cell=25:1, final concentration of antibody=0.01, 0.1, or 1 μg/mL) and incubated at 37° C. for 4 hours. After centrifuging the plate, 50 μL of supernatant was transferred to Luma Plate (manufactured by Perkin-Elmer) and dried. Herein, CPM was measured using a liquid scintillation counter for microplate (TopCount, manufactured by Perkin-Elmer). CPM is the number of count per one minute. The rate of cytotoxicity (Lysis %) was calculated using the following formula.

Lysis %=(Sample CPM−Spontaneous CPM)/(Maximum CPM−Spontaneous CPM)×100

Spontaneous CPM was obtained in the absence of the effector cell and the antibody, and maximum CPM was obtained by adding 1% of NP-40 instead of the effector cell in absence of the antibody.

Figure 3A:
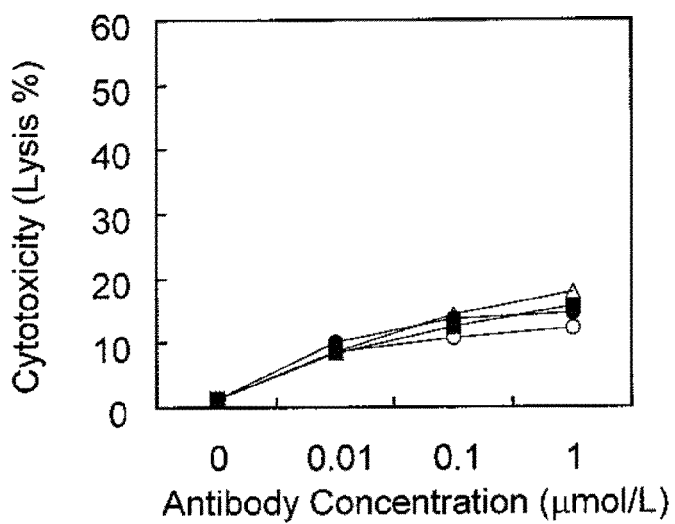
[FIG. 3A]
Figure 3B:
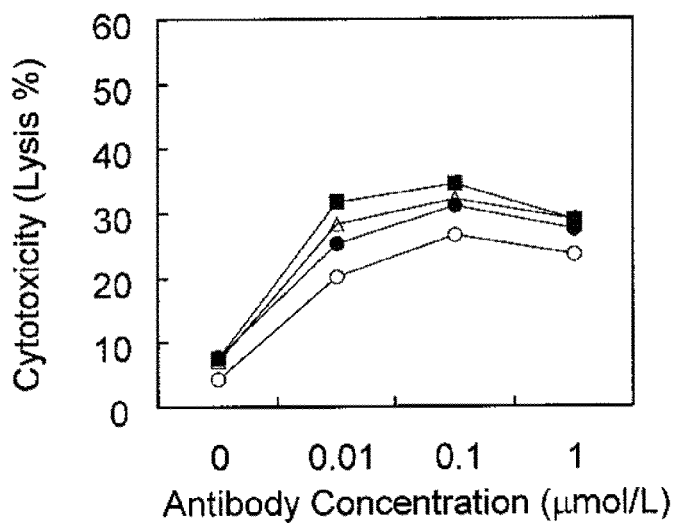
[FIG. 3B]
Figure 3C:
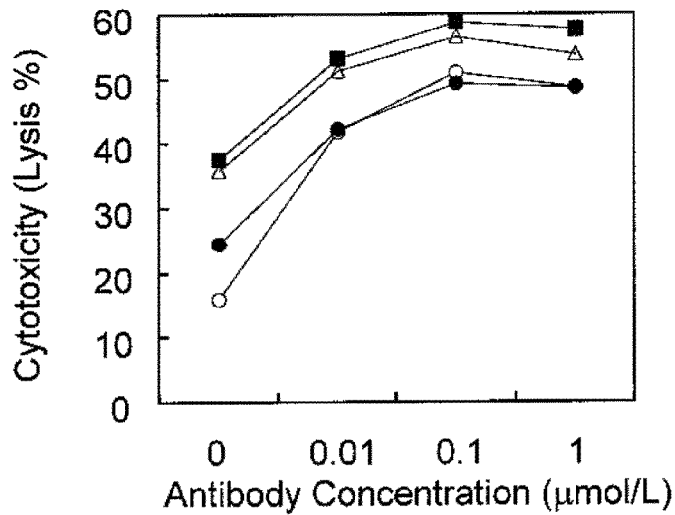
[FIG. 3C]

The result was shown in FIG. 3. As shown in FIG. 3, ADCC activity was clearly enhanced by the treatment of Lenalidomide.

While the invention has been described in detail and with reference to specific embodiments thereof, it will be apparent to one skill in the art that various changes and modifications can be made therein without departing from the spirit and scope thereof.

This application is based on Japanese application No. 2009-209218, filed on Sep. 10, 2009, and U.S. provisional application No. 61/241,558, filed on Sep. 11, 2009, the entire contents of which are incorporated hereinto by reference. All references cited herein are incorporated in their entirety.

Sequence Listing Free Text

SEQ ID NO: 4—description of artificial sequence: synthetic peptide
SEQ ID NO: 5—description of artificial sequence: synthetic peptide
SEQ ID NO: 6—description of artificial sequence: synthetic peptide
SEQ ID NO: 7—description of artificial sequence: synthetic peptide
SEQ ID NO: 8—description of artificial sequence: synthetic peptide
SEQ ID NO: 9—description of artificial sequence: synthetic peptide
SEQ ID NO: 10—description of artificial sequence: synthetic peptide
SEQ ID NO: 11—description of artificial sequence: synthetic peptide
SEQ ID NO: 12—description of artificial sequence: synthetic peptide

What is claimed is:

1. A method for treating cutaneous T cell lymphoma, comprising administering a recombinant antibody which specifically binds to human CC chemokine receptor 4 (hereinafter also referred to as CCR4) and Lenalidomide, wherein said recombinant antibody comprises complementarity determining region (CDR) 1, CDR2 and CDR3 of an antibody heavy chain variable region which comprise the amino acid sequences of SEQ ID NOs: 5, 6 and 7, respectively, and CDR1, CDR2 and CDR3 of an antibody light chain variable region which comprise the amino acid sequences of SEQ ID NOs: 8, 9 and 10, respectively.

2. The method according to claim 1, which comprises simultaneously or sequentially administering the recombinant antibody and Lenalidomide.

3. The method according to claim 1, wherein the tumor is a tumor which expresses CCR4.

4. The method according to claim 1, wherein the recombinant antibody is an antibody having a high antibody-dependent cellular cytotoxicity.

5. The method according to claim 1, wherein the recombinant antibody is a humanized antibody.

6. The method according to claim 5, wherein, in the humanized antibody, the heavy chain variable region of the antibody molecule comprises the amino acid sequence of SEQ ID NO:11, and the light chain variable region of the antibody molecule comprises the amino acid sequence of SEQ ID NO:12.

* * * * *